United States Patent
DelCastillo et al.

(10) Patent No.: US 8,449,500 B2
(45) Date of Patent: May 28, 2013

(54) FLOW PULSATILITY DAMPENING DEVICES FOR CLOSED-LOOP CONTROLLED INFUSION SYSTEMS

(75) Inventors: Jorge DelCastillo, Des Plaines, IL (US); Alp Akonur, Evanston, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 214 days.

(21) Appl. No.: 11/941,840

(22) Filed: Nov. 16, 2007

(65) Prior Publication Data
US 2009/0131859 A1  May 21, 2009

(51) Int. Cl.
*A61M 1/00* (2006.01)

(52) U.S. Cl.
USPC .......................................................... 604/151

(58) Field of Classification Search
USPC ..................... 604/65, 132–157, 31
See application file for complete search history.

(56) References Cited

U.S. PATENT DOCUMENTS

| | | | |
|---|---|---|---|
| 422,936 A | 3/1890 | Hanson |
| 1,627,257 A | 5/1927 | Stevens |
| 2,307,566 A | 1/1943 | Browne |
| 2,315,179 A | 3/1943 | Allender |
| 2,393,838 A | 1/1946 | Tarbox |
| 2,474,512 A | 6/1949 | Bechtold et al. |
| 2,565,374 A | 8/1951 | Kitchel |
| 2,773,455 A | 12/1956 | Mercier |
| 2,927,658 A | 3/1960 | Slater, Jr. |
| 3,252,623 A | 5/1966 | Corbin et al. |
| 3,527,700 A | 9/1970 | Goldhaber |
| 3,658,445 A | 4/1972 | Pulman et al. |
| 3,741,692 A | 6/1973 | Rupp |
| 3,778,195 A | 12/1973 | Bamberg |
| 3,804,107 A | 4/1974 | Kozlov et al. |
| 3,818,934 A | 6/1974 | Borsanyi |
| 3,902,490 A | 9/1975 | Jacobsen et al. |
| 3,974,854 A | 8/1976 | Kurpanek |
| 3,986,956 A | 10/1976 | Anno |
| 4,003,379 A | 1/1977 | Ellinwood, Jr. |
| 4,077,405 A | 3/1978 | Hoerten et al. |

(Continued)

FOREIGN PATENT DOCUMENTS

| | | |
|---|---|---|
| DE | 1960369 A1 | 6/1971 |
| EP | 0 816 677 | 1/1998 |

(Continued)

OTHER PUBLICATIONS

International Search Report and Written Opinion for International Application No. PCT/US2009/030299 mailed on May 29, 2009.

(Continued)

*Primary Examiner* — Nicholas Lucchesi
*Assistant Examiner* — Pritesh Patel
(74) *Attorney, Agent, or Firm* — K&L Gates LLP

(57) ABSTRACT

A flow monitoring infusion system that includes an infusion circuit having a fluid with a pulsatile fluid flow flowing therethrough. The infusion circuit includes a dampening element having a dampening chamber that absorbs the pressure fluctuations of the pulsatile fluid flow to transform the pulsatile fluid flow to a more smooth fluid flow. A fluid flow sensor that measures the flowrate of the more smooth fluid flow is disposed along the infusion circuit downstream of the dampening element.

17 Claims, 3 Drawing Sheets

U.S. PATENT DOCUMENTS

| | | | |
|---|---|---|---|
| 4,081,372 A | 3/1978 | Atkin et al. | |
| 4,107,039 A | 8/1978 | Lindsay, Jr. et al. | |
| 4,191,184 A | 3/1980 | Carlisle | |
| 4,193,068 A | 3/1980 | Ziccardi | |
| 4,209,014 A | 6/1980 | Sefton | |
| 4,258,711 A | 3/1981 | Tucker et al. | |
| 4,264,287 A | 4/1981 | Ishida et al. | |
| 4,293,961 A | 10/1981 | Runge | |
| 4,345,594 A | 8/1982 | Bisera et al. | |
| 4,360,019 A | 11/1982 | Portner et al. | |
| 4,360,324 A | 11/1982 | Ohara et al. | |
| 4,392,791 A * | 7/1983 | Mandroian | 417/379 |
| 4,445,829 A | 5/1984 | Miller | |
| 4,489,750 A | 12/1984 | Nehring | |
| 4,493,706 A | 1/1985 | Bolsanyi et al. | |
| 4,501,583 A | 2/1985 | Troutner | |
| 4,525,165 A | 6/1985 | Fischell | |
| 4,599,165 A | 7/1986 | Chevallet | |
| 4,604,090 A | 8/1986 | Reinicke | |
| 4,610,702 A | 9/1986 | Krantz | |
| 4,653,987 A | 3/1987 | Tsuji et al. | |
| 4,662,829 A | 5/1987 | Nehring | |
| 4,671,792 A | 6/1987 | Borsanyi | |
| 4,673,391 A | 6/1987 | Kondo et al. | |
| 4,684,368 A | 8/1987 | Kenyon | |
| 4,687,423 A | 8/1987 | Maget et al. | |
| 4,687,468 A | 8/1987 | Gianturco | |
| 4,714,462 A | 12/1987 | DiDomenico | |
| 4,728,265 A | 3/1988 | Cannon | |
| 4,741,678 A | 5/1988 | Nehring | |
| 4,744,786 A | 5/1988 | Hooven | |
| 4,767,526 A | 8/1988 | Vantard | |
| 4,838,887 A | 6/1989 | Idriss | |
| 4,871,351 A | 10/1989 | Feingold | |
| 4,954,046 A | 9/1990 | Irvin et al. | |
| 4,969,936 A | 11/1990 | Schweigert et al. | |
| 4,978,338 A | 12/1990 | Melsky et al. | |
| 4,979,441 A | 12/1990 | Welch et al. | |
| 5,053,031 A | 10/1991 | Borsanyi | |
| 5,057,081 A | 10/1991 | Sunderland et al. | |
| 5,088,904 A | 2/1992 | Okada | |
| 5,152,680 A | 10/1992 | Okada | |
| 5,176,644 A | 1/1993 | Srisathapat et al. | |
| 5,183,974 A | 2/1993 | Wilhelm et al. | |
| 5,244,463 A | 9/1993 | Cordner, Jr. et al. | |
| 5,247,434 A | 9/1993 | Peterson et al. | |
| 5,263,935 A | 11/1993 | Hessel | |
| 5,290,158 A | 3/1994 | Okada | |
| 5,387,188 A | 2/1995 | Watson | |
| 5,421,208 A | 6/1995 | Packard et al. | |
| 5,522,998 A | 6/1996 | Polaschegg | |
| 5,544,651 A | 8/1996 | Wilk | |
| 5,554,011 A | 9/1996 | Bales et al. | |
| 5,562,429 A | 10/1996 | Romstad et al. | |
| 5,607,418 A | 3/1997 | Arzbaecher | |
| 5,730,722 A | 3/1998 | Wilk | |
| 5,817,076 A | 10/1998 | Fard | |
| 5,868,168 A | 2/1999 | Mott et al. | |
| 5,871,478 A | 2/1999 | Berrigan | |
| 6,058,958 A | 5/2000 | Benkowski et al. | |
| 6,089,837 A | 7/2000 | Cornell | |
| 6,159,160 A | 12/2000 | Hsei et al. | |
| 6,234,773 B1 | 5/2001 | Hill et al. | |
| 6,280,408 B1 | 8/2001 | Sipin | |
| 6,290,681 B1 | 9/2001 | Brown | |
| 6,305,919 B1 | 10/2001 | Staton et al. | |
| 6,312,409 B1 | 11/2001 | Gross | |
| 6,319,245 B1 | 11/2001 | Berrigan | |
| 6,386,046 B1 | 5/2002 | Mattar | |
| 6,471,686 B1 | 10/2002 | Berrigan | |
| 6,537,268 B1 | 3/2003 | Gibson et al. | |
| 6,558,343 B1 | 5/2003 | Neftel | |
| 6,638,263 B1 | 10/2003 | Theeuwes et al. | |
| 6,669,455 B2 | 12/2003 | Welch | |
| 6,723,062 B1 | 4/2004 | Westberg et al. | |
| 6,746,606 B2 | 6/2004 | Pfeil et al. | |
| 6,837,693 B2 | 1/2005 | Welch | |
| 6,861,033 B2 | 3/2005 | Mullins et al. | |
| 6,997,942 B2 | 2/2006 | Machold et al. | |
| 7,018,361 B2 | 3/2006 | Gillespie, Jr. et al. | |
| 7,018,375 B2 | 3/2006 | Berrigan | |
| 7,025,750 B2 | 4/2006 | Brugger et al. | |
| 7,048,522 B2 | 5/2006 | Bradford, Jr. | |
| 7,150,711 B2 | 12/2006 | Nusser et al. | |
| 7,175,649 B2 | 2/2007 | Machold et al. | |
| 7,208,092 B2 | 4/2007 | Micheli | |
| 7,241,378 B2 | 7/2007 | Ikeda | |
| 7,326,564 B2 | 2/2008 | Lundell et al. | |
| 7,678,070 B2 * | 3/2010 | Kumar et al. | 604/31 |
| 2002/0088752 A1 | 7/2002 | Balschat et al. | |
| 2002/0127736 A1 | 9/2002 | Chou et al. | |
| 2003/0195454 A1 | 10/2003 | Wariar | |
| 2004/0019320 A1 | 1/2004 | Childers et al. | |
| 2004/0082903 A1 | 4/2004 | Micheli | |
| 2005/0038325 A1 | 2/2005 | Moll | |
| 2007/0135758 A1 | 6/2007 | Childers et al. | |
| 2007/0158267 A1 | 7/2007 | Micheli | |
| 2008/0015493 A1 | 1/2008 | Childers et al. | |

FOREIGN PATENT DOCUMENTS

| | | |
|---|---|---|
| GB | 880192 A | 10/1961 |
| GB | 2181494 | 4/1987 |
| GB | 2303925 A | 3/1997 |
| WO | WO8401718 A1 | 5/1984 |
| WO | 2005/025726 | 3/2005 |
| WO | 2006/008866 | 1/2006 |

OTHER PUBLICATIONS

International Search Report and Written Opinion for PCT/US2008/066101 mailed Feb. 12, 2009.

International Search Report and Written Opinion for International Application No. PCT/US2009/047585 dated Feb. 1, 2010.

Non-Final Office Action for U.S. Appl. No. 12/180,324 dated Aug. 12, 2010.

International Search Report and Written Opinion for International Application No. PCT/US2011/023158 dated May 9, 2011.

* cited by examiner

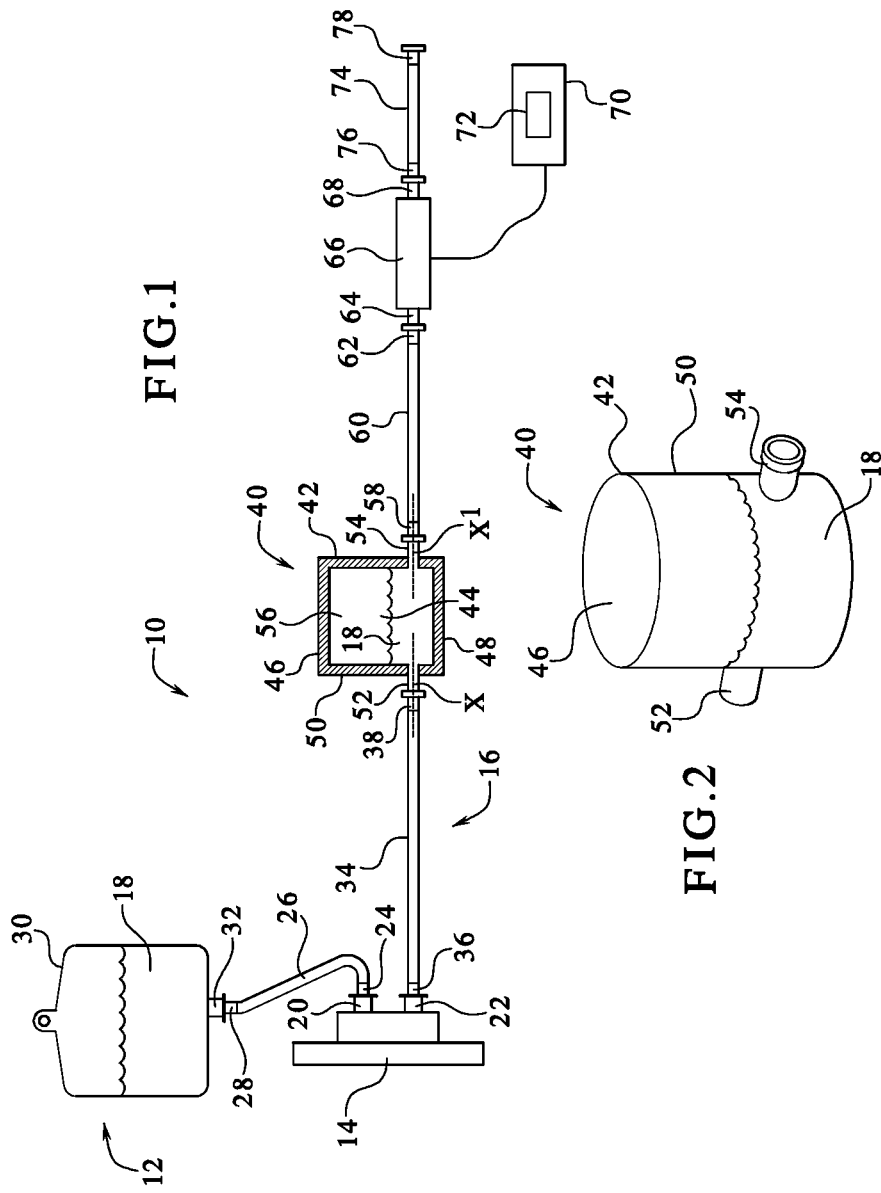

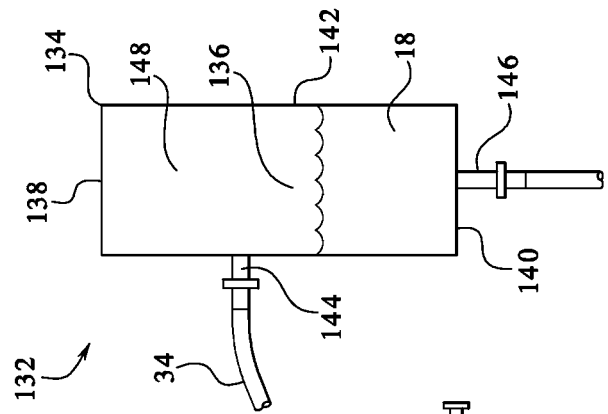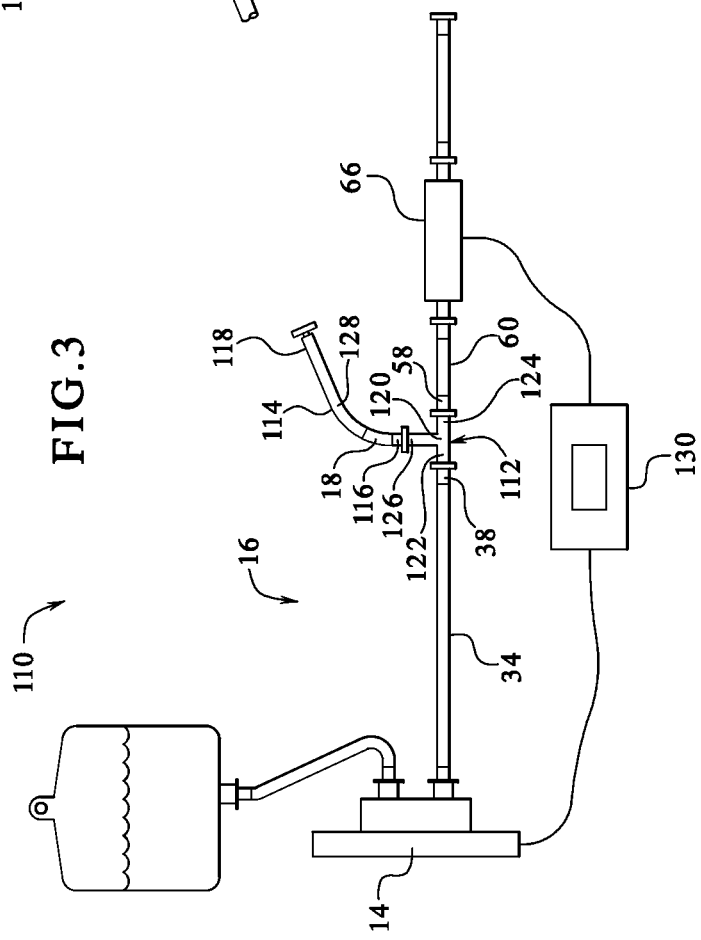

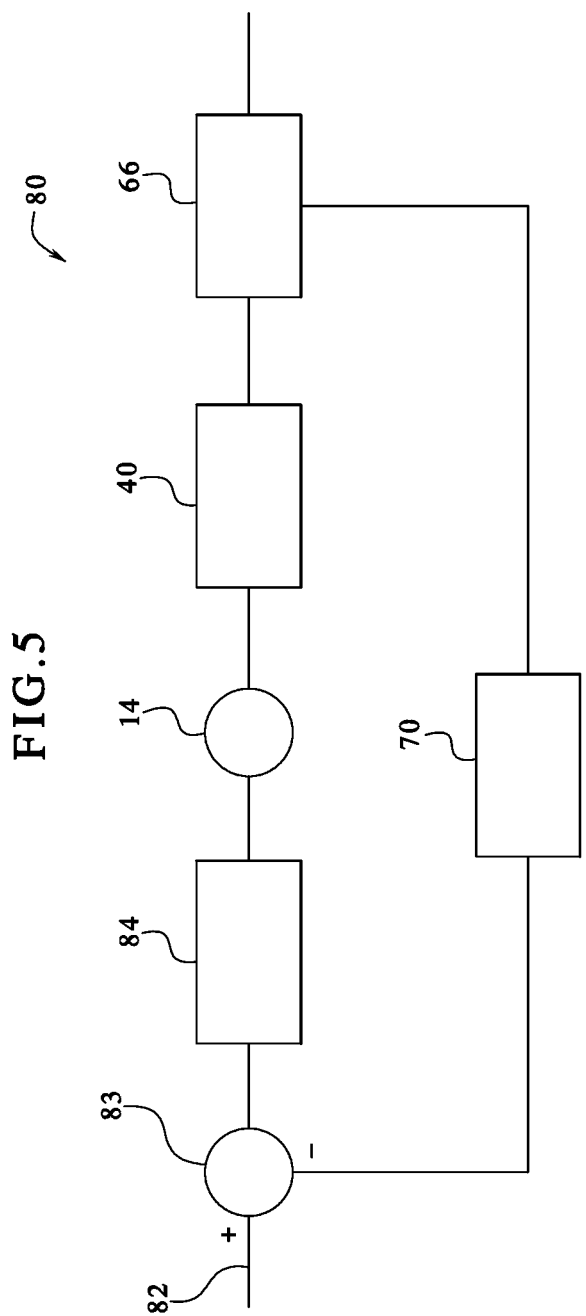

FLOW PULSATILITY DAMPENING DEVICES FOR CLOSED-LOOP CONTROLLED INFUSION SYSTEMS

BACKGROUND

The present disclosure generally relates to medical fluid delivery systems. In particular, the present disclosure relates to devices and methods for transforming a generally pulsatile fluid flow in an infusion system to a smoother or less pulsatile fluid flow.

Liquid medicaments and other complex medical and therapeutic fluids are often administered to patients through infusion therapy. Typically, infusion therapy is accomplished by employing an infusion pump to force fluid through an infusion circuit and into a patient. In certain situations, such as when the infusion of fluid takes place over a long period of time with a patient that is ambulatory, it is desirable to use a disposable infusion system.

Because disposable infusion systems are disposable, such systems typically include relatively simple and inexpensive components. However, one of the difficulties encountered with using relatively simple and inexpensive components is that the components are often not compatible for use with one another. For example, the majority of simple and inexpensive infusion pumps generate a pulsatile or non-continuous fluid flow. Even durable and expensive pumps generate pulsatility. This pulsatile fluid flow is dynamic and has flowrate and pressure fluctuations that change very quickly. Further, most simple and inexpensive fluid flow sensors do not have the temporal resolution or the ability to sense and calculate the flowrate of a pulsatile fluid flow. The incompatibility of these components creates an obstacle to producing economical disposable infusion systems that have the ability to monitor the fluid flowrate within the infusion circuit.

In many infusion therapy applications a fluid is required to be administered to the patient at a certain fluid flowrate to be therapeutically effective. For example, in some applications, if the fluid is infused too slowly, the intended therapeutic effect may be diminished or totally non-existent. In other applications, infusion of a fluid into the body at too high a rate can create a dangerous or overdose situation. Thus, in a number of infusion therapy applications it is important for the user to be able to quickly and accurately determine the rate of fluid flow through the system, so that the flowrate can be monitored and adjusted as needed.

In those instances in which it is important for the user to be able to determine flowrate, a disposable infusion set will often include either an infusion pump that generates a smooth fluid flow or a flow sensor that has the ability to monitor and calculate the flowrate of a pulsatile or non-continuous fluid flow. One of the disadvantages of using a smooth flow generating infusion pump or a flow sensor that can monitor pulsatile flow is that both of those components are relatively expensive and add appreciably to the overall cost of the disposable infusion set. In addition to increased cost, system components that are capable of achieving high resolution measurements often require complex circuitry, hardware and software architecture.

SUMMARY

The present disclosure provides an infusion system that includes a dampening element, which transforms a generally non-continuous or pulsatile flow of fluid within the infusion system into a generally smoother or less pulsatile fluid flow. The incorporation of a dampening element in to an infusion system provides a variety of benefits. For example, the transformation of a generally pulsatile fluid flow into a smoother fluid flow allows a relatively inexpensive fluid flow sensor, which does not have the temporal resolution to sense and calculate flowrate of a pulsatile flow of fluid, to be used to monitor and adjust such fluid flow. The ability to employ a relatively inexpensive flow sensor decreases the overall cost of the infusion system appreciably.

In general, the dampening element is disposed at a location along the fluid pathway of an infusion system and receives a fluid having a pulsatile fluid flow from a fluid source upstream of the dampening element. The dampening element includes a dampening chamber having a compressible gas, such as air, located therein. When the pulsatile fluid flow enters the dampening element, the gas within the chamber compresses to absorb the pressure fluctuations of the pulsatile fluid flow, thereby transforming the pulsatile fluid flow into a smoother or less pulsatile fluid flow. The smoother flow of fluid exits the dampening element and flows downstream through the remaining portion of the infusion system.

One aspect of the present disclosure relates generally to a flow monitoring infusing system that includes a fluid pathway containing a fluid that has a generally pulsatile fluid flow. The infusion system also includes a dampening chamber disposed along the fluid pathway. The dampening chamber contains a compressible gas that absorbs the pressure fluctuations of the pulsatile fluid flow to transform the pulsatile fluid flow to smoother fluid flow. The infusion system further includes a fluid flow sensor disposed along the infusion circuit downstream of the dampening element. The flow sensor measures the flowrate of the smooth fluid flow. In an embodiment, the flow sensor is a relatively inexpensive flow sensor that is intended to measure a generally smooth flow of fluid.

Another aspect of the present disclosure generally relates to infusion systems that transform a generally pulsatile fluid flow to a more smooth fluid flow. The infusion system includes an infusion pathway and an infusion pump that generates a generally pulsatile flow of fluid through the pathway. The infusion system also includes a generally tubular element defining a dampening chamber that is in fluid communication with the pathway. The dampening chamber contains a compressible gas that absorbs the pressure fluctuations of pulsatile fluid flow. The system also includes a flow sensor that monitors the flow of the smoothened fluid.

A further aspect of the present disclosure relates to a method for controlling the rate of fluid flow through an infusion system. The method includes flowing a pulsatile fluid flow through the infusion system. The pulsatile fluid flow is transformed into a smoothed fluid flow which is measured to determine the actual fluid flowrate. The actual fluid flowrate is compared to a desired fluid flowrate and the flow of pulsatile fluid is adjusted until the actual fluid flowrate is equal to the desired fluid flowrate.

Additional features and advantages are described herein, and will be apparent from, the following Detailed Description and the figures.

BRIEF DESCRIPTION OF THE FIGURES

FIG. 1 is a side view of one embodiment of an infusion system according to the present disclosure;

FIG. 2 is a perspective view of the dampening element shown in FIG. 1;

FIG. 3 is a side view of another embodiment of an infusion system according to the present disclosure;

FIG. 4 is an elevation view of another embodiment of a dampening member of the present disclosure; and FIG. 5 is a schematic illustration of one embodiment of a closed-loop control system of the present disclosure.

DETAILED DESCRIPTION

Referring now to the drawings and in particular to FIG. 1, an infusion therapy system or set 10 for infusing fluids, such as medicaments or other therapeutic fluids, into a patient is provided. The infusion therapy system 10 in an embodiment is a disposable infusion system that includes relatively inexpensive component parts. In the embodiment shown, the infusion therapy system 10 includes a fluid supply 12, an infusion pump 14 and a fluid pathway 16. In general, the infusion pump 14 pumps fluid 18 from the fluid supply 12, through the infusion pathway 16, to an infusion device (not shown) that delivers the fluid to a patient. The infusion device can be any number of infusion devices, such as a catheter, implantable port, intravenous delivery device, shunt or other mechanism that interfaces with the patient to deliver fluid.

The infusion pump 14 is a pump that generates a pulsatile fluid flow having pressure fluctuations, such as a micro-diaphragm or a peristaltic pump. For example, the pump can for example be a micro-diaphragm pump provided by thinXXS Microtechnology AG, Zweibrücken, Germany. The pump itself can be disposable. Alternatively, the fluid carrying components of the pump are disposable. These types of pumps are often small in size, generally lightweight and relatively inexpensive. The pump 14 includes an inlet port 20 for receiving fluid and an outlet port 22 for expelling fluid. The inlet port 20 of the infusion pump 14 is connected to the distal end portion 24 of a fluid supply conduit 26, and the proximal end portion 28 of the fluid supply conduit 26 is connected to fluid supply 12. The connection between the fluid supply conduit 26 and the pump 14, and other connections of components described herein, can be any suitable type of permanent or removable connection known to those skilled in the art, such as a male-female luer type connection or an integral connection.

The fluid supply 12 may include a flexible dispensing bag 30 containing a fluid 18 to be infused into the patient. The dispensing bag 30 in an embodiment is made from a polymeric material and includes outlet port 32 that is connected to the proximal end portion 28 of fluid supply conduit 26. The dispensing bag 30 supplies the fluid 18 through the fluid supply conduit 26 to the infusion pump 14.

Infusion pathway 16 provides a fluid path from the pump 14 to an infusion device (not shown). Infusion pathway 16 can include a first fluid conduit 34 that has a proximal end portion 36 and a distal end portion 38. Proximal end portion 36 of first fluid conduit 34 is connected to outlet port 22 of infusion pump 14 and receives a pulsatile flow of fluid from the infusion pump. For example, the rollers of a race of a peristaltic pump create a generally pulsatile flow. The back and forth motion of a membrane or diaphragm in a membrane pump also creates non-continuous or pulsatile flow.

A pulsatility dampening device or element 40 is disposed along infusion pathway 16 at a location that is downstream of the infusion pump 14. Distal end portion 38 of first fluid conduit 34 is connected to dampening element 40. Dampening element 40 receives the pulsatile fluid flow and transforms it into a smoother or more continuous fluid flow.

Dampening element 40 shown in FIGS. 1 and 2 has a generally cylindrical body 42 defining a dampening chamber 44. Alternatively, element 40 has a rectangular or other suitable shape. In one embodiment, the dampening chamber has a volume between about eight milliliters ("ml") and thirty ml. The dampening element body 42 includes a top wall 46, a bottom wall 48 and a generally cylindrical sidewall 50. Dampening element 40 can be made of a suitable polymeric material, such as a polymer material that does not react with the fluid being infused. Dampening element 40 includes an inlet port 52 and an outlet port 54 extending through sidewall 50 of the dampening element. Inlet port 52 and outlet port 54 are in fluid communication with dampening chamber 44.

In an embodiment, inlet port 52 and outlet port 54 are generally aligned so that the fluid flow path through dampening element 40 is substantially straight or linear. In the illustrated embodiment, inlet port 52 includes a central axis X and outlet port 54 includes a central axis Y. Inlet port 52 and outlet port 54 are disposed along the sidewall 50 so that axis X and axis Y are generally coaxial. Alternatively, inlet port 52 and outlet port 54 could be disposed along the sidewall 50 so that the inlet port and the outlet port are not aligned. For example, the outlet port 54 could be disposed along the sidewall 50 so its central axis Y, is not coaxial with axis X of the inlet port 52, or the inlet port and outlet port can be positioned so that the axis X and axis Y lay in different planes.

Inlet port 52 of dampening element 40 is connected to distal end portion 38 of first fluid conduit 34 so that dampening chamber 44 is in fluid communication with fluid path 16. As fluid 18 is infused into the system, fluid resistance and backpressure on the downstream side of dampening element 40 causes an increase of fluid pressure within the system. This increase in fluid pressure causes fluid 18 to partially fill the dampening chamber 44 so that the fluid level is above or covers inlet port 52 and outlet port 54.

As fluid 18 fills dampening chamber 44, the fluid traps and compresses gasses contained in space 56 above the fluid. The gas can be air or an otherwise compressible gas. As explained above, the pump provides a pulsatile or non-continuous fluid flow, which periodically increases and decreases in pressure at a regular interval as the fluid flows through the infusion system. This pulsatile fluid flow enters dampening chamber 44, and as the pressure of fluid 18 periodically increases, the gas within chamber 44 compresses to absorb the increases in pressure. This produces a smoother or more continuous flow of fluid that flows out of outlet port 54. In other words, the gas within space 56 provides a dampening quality wherein the pressure fluctuations of the pulsatile flow are absorbed by the gas to produce a less pulsatile or smoother flow of fluid out of the outlet port 54.

The dampening quality of the chamber and the smoothness of the fluid provided by dampening element 40 can depend on a variety of variables, such as the volume of the dampening chamber, the viscosity of the infusion fluid, the compressibility of the gas located within the dampening chamber and the backpressure within the fluid system. By adjusting these variables the dampening chamber can be optimized for a particular infusion application. Practically, the volume of the chamber is the mainly adjustable parameter. The viscosity of the fluid is set by the liquid to be infused. The backpressure in the system depends on the viscosity and geometrical properties of other disposable components within the circuit.

A proximal end portion 58 of a second fluid conduit 60 is connected to outlet 54 of dampening element 40 so that second fluid conduit 60 receives a generally smooth or continuous flow of fluid from the dampening element. A distal end portion 62 of second fluid conduit 60 is connected to an inlet port 64 of a flow monitor or flow sensor 66 that is disposed along the infusion circuit at a location downstream of dampening element 40. As the fluid flows through flow sensor 66 towards an outlet port 68 of the flow sensor, the flow sensor detects the rate of fluid flow. Because the dampening member has transformed the fluid flow to a smoother flow, a flow sensor for measuring pulsatile fluid flow is not needed, and flow sensor 66 can be of the type that is generally employed to monitor and calculate the flowrate of a generally smooth or slightly pulsatile flow. For example, the flow sensor can be an optical, laser or heat pulse, time-of-flight type non-invasive flowrate sensor. While non-invasive sensors are advantageous for sterility purposes, they are not critical for the present disclosure. Invasive flow sensors, such as positive displacement flow sensors, can be used alternatively.

In an embodiment, flow sensors that are generally only used to sense smooth fluid flow can be employed because they are relatively inexpensive when compared to flow sensors that have the ability to sense and monitor the flowrate of a fluid having a pulsatile flow. Further, it should be understood that these relatively inexpensive smooth fluid flow sensors are normally incompatible for use with the pulsatile fluid flow generating pumps described above.

After the fluid flows out of flow sensor 66, the fluid enters into a third fluid conduit 74 having a proximal end portion 76 connected to flow sensor outlet 68. The fluid flows through third fluid conduit 74 and into an infusion device (not shown, e.g., catheter or cannula) that is connected to distal end portion 78 of the third fluid conduit 74. The infusion device delivers the fluid to the patient.

In one embodiment, flow sensor 66 is connected to a processing unit 70 that receives a signal from the flow sensor and calculates the flowrate. The processing unit 70 can include a display device 72, such as a liquid crystal display, for indicating the flowrate to the user. Upon receiving flowrate information, the user may then use this information to adjust the pump as necessary so as to optimize and achieve the desired flowrate.

Optionally, processing unit 70 communicates with and controls infusion pump 14 with a closed-loop control, which adjusts the infusion pump actuator based on sensed flowrate information to optimize the flowrate. FIG. 5 illustrates one embodiment of a closed-loop control system 80 that can be employed to optimize the flowrate of fluid in the infusion system. Closed-loop control system 80 includes an input 82 to a summing junction 83. The user sets input 82 at a control unit, such as control unit 130 shown in FIG. 3. The input represents a desired flowrate for a particular infusion therapy application. Input 82 operates or is fed to a pump speed controller 84. Pump speed controller 84 is operably connected to and controls the pumping speed or pump settings of infusion pump 14.

In one embodiment, the pump speed of pump 14 is controlled by the amount of voltage or current that pump speed controller 84 supplies to pump 14. Input 82 tells pump speed controller 84 what initial voltage or current to use. Pump speed controller 84 supplies this initial amount of voltage or current to pump 14. The increase in voltage or current increases the pumping speed of pump 14, which in turn increases flowrate. Likewise, when input 82 receives a directive to decrease pump speed, pump speed controller 84 decreases the amount of voltage or current supplied to pump 14, which decreases the pumping speed and the flowrate.

As explained above, pump 14 provides a pulsatile or non-continuous flow of fluid to dampening element 40. Dampening element 40 converts the fluid flow into a smoother flow and the fluid flows to flow sensor 66. Flow sensor 66 senses the actual flowrate and sends a flowrate signal to processor 70. Processor 70 compares actual flowrate from sensor 66 to the inputted flowrate set at 82. If actual flowrate equals set flowrate, processor 70 does not modify input signal 82 at summer 83. If processor 70 determines the flowrate needs to be adjusted processor 70 communicates the needed adjustment to summer 83, which modifies input 82 to produce a modified signal to controller 84, which adjusts voltage or currents to pump 14 accordingly. Processor 70 can use only one or more or all of a proportional, integral and differential ("PID") gain to modify input 82 at summer 83. PID control is known in the art. Closed-loop control 80 continuously monitors and adjusts the pump speed setting to have the sensed flowrate to the desired flowrate.

It is worth noting that a flowrate signal of a smooth flowing fluid sensed at sensor 66 is used to control an input to a generally pulsatile or non-continuous pump. Any one or more of the PID gains can be set empirically to optimize the feedback to account for the pulsatile/non-pulsatile mismatch. The resulting system is an inexpensive but accurate system.

FIG. 3 illustrates another embodiment of an infusion system 110, which is generally similar to infusion system 10 illustrated in FIG. 1. The infusion system 110 includes infusion pump 14, infusion pathway 16 and flow sensor 66. In this embodiment, the damping element 112 includes a generally tubular shaped dampening chamber 114 having a distal end 116 and a closed proximal end 118. The distal end portion 116 is in fluid communication with the fluid pathway. Dampening chamber 114 also extends in a generally perpendicular direction to the flow of fluid through the fluid passageway. The tubular dampening chamber 114 may be made of a polymeric flexible material. For example, the dampening chamber can be a length of a flexible tubing line. In one embodiment, the tubular dampening chamber 114 has a diameter of about 0.125 inches (3.2 mm) to about 0.25 inches (6.4 mm), a length of about 2 inches (5.1 cm) to about 10 inches (25.4 cm) and a volume of about 1 ml to about 3 ml.

In the illustrated embodiment, dampening element 112 includes a T-shaped three way connector 120 having a first port 122 in communication with distal end portion 38 of first fluid conduit 34, a second port 124 in communication with proximal end portion 58 of second fluid conduit 60 and a third port 126 in communication with tubular shaped dampening chamber 114. As fluid is infused, the resistance and backpressure down stream of the dampening element 112 causes fluid 18 to partially fill a portion of the tubular dampening chamber 114. As fluid fills dampening chamber 114, the fluid traps and compresses gas in space 128 above the fluid. Similar to the previous embodiment, as fluid pressure increases during the natural fluctuation of the pulsatile fluid flow, the increased pressure of the fluid is exerted against the gas in space 128. The gas compresses to absorb the increased fluid pressure and to convert the pulsatile fluid flow to a smoother or more continuous flow. The smoother flow of fluid exits out of outlet port 124 and flows through second fluid conduit 60 to flow sensor 66. Flow sensor 60 measures the fluid rate of the smooth fluid flow in a similar fashion as described above.

In an alternative embodiment, the first fluid conduit 34, second fluid conduit 60 and dampening chamber 114 could be connected to different ports of the T-shaped connector. For example, the dampening chamber 114 can be connected to the first port 122 of the T-shaped connector and the first fluid conduit 34 can be connected to the third port 126, or the dampening chamber 114 can be connected to the second port 124 and the second fluid conduit 60 can be connected to the third fluid port 126. While the dampening chamber can be connected to different ports, the dampening chamber should be either vertical to the fluid path or above the fluid path so that gas within the fluid chamber does not enter fluid being infused.

FIG. 4 illustrates another embodiment of a dampening element 132 that can by used in an infusion system to transform a pulsatile fluid flow to a generally smooth fluid flow. The dampening element 132 has a generally cylindrical body 134 defining a damping chamber 136. The body has a top wall 138, a bottom wall 140 and a circumferential sidewall 142. The dampening element 132 includes an inlet port 144 located through the sidewall 142 and an outlet port 146 located through the bottom wall 140. The inlet port 144 is connected to and receives a pulsatile flow of fluid from the first fluid conduit 34 into the dampening chamber 136. During the infusion therapy operation, the dampening chamber 136 is partially filled with fluid 18. Similar to the previous embodiments, the dampening chamber 136 has a space 148 that is occupied by a compressible gas that absorbs the pressure fluctuations of the pulsatile fluid flow.

The pulsatile fluid flow enters inlet port 144 from first fluid conduit 34. In the dampening chamber 136, the gas located within the space 148 absorbs the pressure fluctuations of the pulsatile fluid flow, transforming the fluid flow into a less pulsatile or smoother fluid flow. The smoother flow of fluid exits the dampening chamber 136 through the outlet 148 and flows into the second fluid conduit 60.

In the embodiments illustrated herein for dampening elements 40, 112 and 132, the dampening elements should be oriented as shown, such that the liquid/air interface is located above the respective outlet of the dampening chamber. For example, outlet 54 is located elevationally below the liquid/air interface of dampening element 40 in FIGS. 1 and 2. Outlet port 124 is located elevationally below the liquid/air interface of dampening element 112 in FIGS. 1 and 2. Outlet port 146 is located elevationally below the liquid/air interface of dampening element 132 in FIG. 4. In an alternative embodiment, any of dampening elements 40, 112 and 132 can have a flexible membrane or diaphragm that separates the liquid from the gas, the liquid side of the element being fully primed to the flexible membrane or diaphragm. The membrane and the compressibility of the gas here dampens the pulsatility of the fluid being pumped. The membrane also allows the dampening elements 40, 112 and 132 to be mounted in different orientations, which would allow an infusion pump incorporating any of the dampening elements to also be mounted in different orientations.

Infusion system 110 using any of the dampening elements discussed herein includes a control unit 130, which is in communication with the flow sensor 66 and the infusion pump 14. Using the control system of FIG. 5, the control unit 130 can be employed to create a closed-loop controlled infusion system that optimizes the flowrate of fluid through the infusion system. For example, a user enters a desired flowrate into the control unit 130. The control unit 130 communicates with the infusion pump 114 to set the pump to pump fluid at the desired flowrate. The control unit 130 receives information from the flow sensor 66 regarding the actual flowrate through the infusion circuit, and then processes the information to calculate the actual flowrate. The control unit 130 can include a PID control discussed above that compares the actual flowrate to the desired flowrate and adjusts infusion pump 14 as needed until the actual flowrate is equal to the desired flowrate.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A flow monitoring infusing system, comprising:
   a liquid pathway for containing a liquid pumped at a non-continuous fluid flow;
   a dampening chamber in communication with the liquid pathway, the dampening chamber configured to hold a compressed gas that absorbs pressure fluctuations of the non-continuous fluid flow to smoothen the non-continuous fluid flow, wherein the compressed gas is in direct fluid communication with the pumped liquid; and
   a fluid flow sensor disposed along the liquid pathway downstream of the dampening chamber to measure the flowrate of the smoothened fluid flow.

2. The infusion system of claim 1, which includes a pulsatile infusion pump in communication with the fluid pathway for providing a non-continuous fluid flow.

3. The infusion system of claim 2, wherein the pulsatile infusion pump is selected from the group consisting of a membrane pump and a peristaltic pump.

4. The infusion system of claim 1, wherein the dampening chamber includes a generally cylindrical or rectangular body shape.

5. The infusion system of claim 1, wherein the dampening chamber is a length of tubing extending from the fluid pathway.

6. The infusion system of claim 1, wherein the dampening chamber has a volume between about 8 ml and about 30 ml.

7. The infusion system of claim 1, wherein the gas includes air.

8. The infusion system of claim 1, further including a closed-looped control system configured to optimize the flowrate.

9. The infusion system of claim 6, wherein the closed-looped control system includes a PID controller.

10. An infusion system comprising:
    a fluid pathway;
    an infusion pump for pumping a non-continuous flow of fluid through the fluid pathway;
    a generally tubular shaped member defining a chamber that is in communication with the fluid pathway, the chamber containing a compressed gas that absorbs pressure fluctuations of the non-continuous fluid to smoothen the non-continuous flow, wherein the compressed gas is in direct fluid communication with the non-continuous flow of fluid;
    a fluid flow sensor disposed along the fluid pathway downstream of the tubular shaped member, the flow sensor configured to measure a flowrate of the smoothened fluid flow, the fluid pathway extending from the pump, through the fluid sensor and downstream from an outlet of the fluid sensor; and
    a control member operable with the flow sensor and the infusion pump, the control member configured to receive flowrate information from the flow sensor and to adjust the infusion pump based on the flowrate information.

11. The infusion system of claim 10, wherein the generally tubular shaped member is operably connected to the fluid pathway by a T-shaped connector.

12. The infusion system of claim 10, wherein the generally tubular shaped element comprises a length of flexible tubing.

13. The infusion system of claim 10, wherein the tubular shaped member extends in a generally perpendicular direction from the fluid pathway.

14. The infusion system of claim 10, wherein the chamber has a volume between about 8 ml and about 30 ml.

15. The infusion system of claim 10, wherein the control member includes a PID controller.

16. The infusion system of claim 10, wherein the infusion pump is selected from the group consisting of a membrane pump and a peristaltic pump.

17. A flow monitoring infusing system, comprising:
- a fluid pathway for containing a fluid pumped at a non-continuous fluid flow;
- a dampening chamber in communication with the fluid pathway, the dampening chamber configured to hold a gas that absorbs pressure fluctuations of the non-continuous fluid flow to smoothen the non-continuous fluid flow, wherein the compressed gas is in direct fluid communication with the pumped fluid; and
- a fluid flow sensor disposed along the fluid pathway downstream of the dampening chamber to measure the flow-rate of the smoothened fluid flow that flows through the fluid flow sensor.

* * * * *